US009375707B2

(12) United States Patent
Ganhy et al.

(10) Patent No.: US 9,375,707 B2
(45) Date of Patent: Jun. 28, 2016

(54) CATALYST SUPPORT AND PROCESS FOR THE PREPARATION THEREOF

(71) Applicants: Jean-Pierre Ganhy, Brussels (BE); Armin T. Liebens, Braine L'Alleud (BE)

(72) Inventors: Jean-Pierre Ganhy, Brussels (BE); Armin T. Liebens, Braine L'Alleud (BE)

(73) Assignee: SOLVAY SA, Brussels (BE)

( * ) Notice: Subject to any disclaimer, the term of this patent is extended or adjusted under 35 U.S.C. 154(b) by 203 days.

(21) Appl. No.: 14/050,823

(22) Filed: Oct. 10, 2013

(65) Prior Publication Data

US 2014/0142329 A1 May 22, 2014

Related U.S. Application Data

(62) Division of application No. 12/674,202, filed as application No. PCT/EP2008/061239 on Aug. 27, 2008, now abandoned.

(30) Foreign Application Priority Data

Aug. 30, 2007 (EP) .................................... 07115255

(51) Int. Cl.
| | |
|---|---|
| *B01J 29/068* | (2006.01) |
| *B01J 21/12* | (2006.01) |
| *B01J 23/38* | (2006.01) |
| *B01J 23/44* | (2006.01) |
| *B01J 23/89* | (2006.01) |
| *B01J 37/02* | (2006.01) |
| *C01B 15/023* | (2006.01) |
| *C07C 37/055* | (2006.01) |

(52) U.S. Cl.
CPC ............... *B01J 29/068* (2013.01); *B01J 21/12* (2013.01); *B01J 23/38* (2013.01); *B01J 23/44* (2013.01); *B01J 23/8906* (2013.01); *B01J 37/0201* (2013.01); *C01B 15/023* (2013.01); *C07C 37/055* (2013.01)

(58) Field of Classification Search
None
See application file for complete search history.

(56) References Cited

U.S. PATENT DOCUMENTS

| | | | | |
|---|---|---|---|---|
| 2,285,314 A * | 6/1942 | Ahlberg | ................... | B01J 21/12 502/263 |
| 2,287,917 A | 6/1942 | Thomas et al. | | |
| 3,034,994 A | 5/1962 | Braithwaite et al. | | |
| 3,560,370 A | 2/1971 | Billon et al. | | |
| 4,218,308 A | 8/1980 | Ikuo et al. | | |
| 4,226,743 A * | 10/1980 | Seese | ....................... | B01J 21/12 502/235 |
| 4,422,959 A * | 12/1983 | Lawson | ................. | C10G 47/12 208/111.2 |
| 4,431,749 A | 2/1984 | Hettinger, Jr. et al. | | |
| 4,499,197 A * | 2/1985 | Seese | ....................... | B01J 21/12 502/235 |
| 4,803,063 A * | 2/1989 | Pralus | .................. | C01B 15/023 423/588 |
| 4,837,193 A | 6/1989 | Akizuki et al. | | |
| 4,988,659 A * | 1/1991 | Pecoraro | ............... | C10G 11/04 502/235 |
| 5,413,739 A * | 5/1995 | Coleman | .................. | C09K 9/00 252/511 |
| 5,413,789 A | 5/1995 | Hagiwara et al. | | |
| 5,625,013 A * | 4/1997 | Mueller | .................. | C08F 10/00 502/228 |
| 6,485,702 B1* | 11/2002 | Lujano | ..................... | B01J 20/02 423/328.1 |
| 2002/0013375 A1* | 1/2002 | Roy-Auberger | ....... | C10G 2/332 518/715 |
| 2004/0092383 A1* | 5/2004 | Timken | .................... | B01J 21/12 502/63 |
| 2010/0248950 A1* | 9/2010 | Morell | ..................... | B01J 21/08 502/239 |

FOREIGN PATENT DOCUMENTS

| | | |
|---|---|---|
| EP | 0935996 A2 | 8/1999 |
| FR | 2614015 A1 | 10/1988 |
| GB | 392954 A | 5/1933 |
| GB | 396712 A | 8/1933 |
| GB | 596162 A | 12/1947 |
| GB | 619231 A | 3/1949 |
| GB | 744467 A | 2/1956 |
| GB | 790476 A | 2/1958 |
| GB | 805960 A | 12/1958 |
| GB | 1178594 A | 1/1970 |
| GB | 1182929 A | 3/1970 |
| GB | 1218080 A | 1/1971 |
| GB | 1223878 A | 3/1971 |
| JP | 07-060124 | 6/1995 |
| KR | 2004 0073712 A | 8/2004 |
| WO | WO 2008/122503 A1 | 10/2008 |
| WO | WO 2009/027439 A3 | 3/2009 |

OTHER PUBLICATIONS

"Sodium Aluminate Solution (Coogee)," CoogeeChemicals Safety Data Sheet, Jul. 13, 2009.
Dorémieux-Morin, Claudine, et al., "Multinuclear high-resolution solid-state nuclear magnetic resonance studies of amorphous silica-aluminas," Applied Catalysis, vol. 77, No. 1, Oct. 1, 1991, pp. 149-161.

(Continued)

*Primary Examiner* — Melvin C Mayes
*Assistant Examiner* — Colette Nguyen (57) ABSTRACT

An amorphous catalyst support comprising at least a first oxide selected from the group consisting of: silica, germanium oxide, titanium oxide, zirconium oxide or mixtures thereof, preferably silica gel beads or diatomaceous earth; a group 3 metal oxide; and anions in an amount not greater than 10% by weight of the catalyst support; wherein the group 3 metal oxide is incorporated in the first oxide structure at the molecular level. The catalyst support is prepared by (a) mixing the first oxide, with an anhydrous source of the group 3 metal oxide, and water, at a pH above 11, thus forming a suspension, (b) washing the catalyst support with water, (c) separating the catalyst support from the water, and (d) optionally drying and/or calcining the catalyst support. A catalyst based on such a support has improved catalytic properties.

20 Claims, 4 Drawing Sheets

(56) References Cited

OTHER PUBLICATIONS

Flynn, Daniel J., "Impurities in Water," Nalco Water Handbook, 3rd Ed., Feb. 3, 2010.

Kato, Yuko, et al., "Quantification of aluminum coordination in alumunia and silica-alumina by Al K-edge Xanes," Physical Chemistry Chemical Physics, Royal Society of Chemistry, Cambridge, GB, vol. 3, No. 10, Apr. 20, 2001.

Lewis, Richard J. et al., "Hawley's Condensed Chemical Dictionary," 15th Ed., Jan. 1, 2007, John Wiley & Sons.

Luo Xiaoming, et al., "A study on the crystallization of binderless zeolite X," Studies in Surface Science and Catalysis, Elsevier B.V. NL., vol. 105, Jan. 1 1997, pp. 293-300.

Patterson, R.E., "Silica, Introduction," Mar. 1, 2003, Kirk Othmer Encyclopedia of Chemical Technology, pp. 1-26.

EPO Examination Report issued Aug. 27, 2014, for European Patent Application No. 08787531.6.

Third Party Observations, dated Dec. 6, 2010, for European Patent Application No. EP 2188049/08787531.6.

Weckhuysen, Bert M., et al. "A Quantitative Diffuse Reflectance Spectroscopy Study of Supported Chromium Catalysts," Journal of Physical Chemistry, American Chemical Society, US, vol. 97, Feb. 1, 1993, pp. 4756-4763.

Weckhuysen, Bert M., et al., "Redox behavior and dispersion of supported chromium catalysts," Journal of Physical Chemistry, American Chemical Society, US, vol. 99, Jan. 1, 1995, pp. 320-326.

Weckhuysen, Bert M., et al:, "Diffuse reflectance spectroscopy study of the thermal genesis and molecular structure of chromium-supported catalysts," Journal of Physical Chemistry, American Chemical Society, US, vol. 98, Jan. 1, 1994, pp. 579-584.

Wikipedia "Diatomaceous earth," printed from the Internet address: http://en.wikipedia.org/wiki/Diatomaceous_earth, May 12, 2012, 9 pages.

Translation and comments of Japanese Office Action issued Mar. 7, 2013, in corresponding Japanese application No. 2010-522362.

Written Opinion of the International Searching Authority, mailed Jul. 23, 2009, for corresponding International application No. PCT/EP2008/061239.

Olaf Deutschmann, Helmut Knozinger, Karl Lochloefl, Thomas Turek, "Heterogeneous Catalysis and Solid Catalysts" ULLMANN's Encyclopedia of Industrial Chemistry" DOI: 10.1002/14356007.a05_313.pub2, Article Online Posting Date: Apr. 15, 2009, p. 42-44", 110 pgs.

Bin Xu, Carsten Sievers, Johannes A. Lercher, J.A. Rob Van Veen, Patricia Giltay, Roel Prins, & Jeroen A. Van Bokhoven, "Strong Bronsted Acidity in Amorphous Silica-Aluminus", Journal of Physical Chemistry, vol. 111, No. 32, 2007, p. 12075-12079, XP002465035, paragraph [002.]; figure 3.

Elvers et al., Editors, Ullmann's Encyclopedia of Industrial Chemistry—5th Edition, vol. A13, 'High Performance Fibers from Imidazole and Derivatives', p. 447-457, 1989—13 pp.

Anna Omegna, Jereon A. Van Bokhoven & Roel Prins: "Flexible Aluminum Coordination in Alumino-Silicates, Structure of Zeolite H-USY and Amorphous Silica-Alumina", Journal of Physical Chemistry, vol. 107, No. 34, Aug. 2, 2003, pp. 8854-8860, XP002465036; paragraph [02.1], [04.2]; figure 3.

Chen et al., "Toward the aluminum coordination in dealuminated mordenite and amorphous silica-alumina: A high resolution 27 Al MAS and MQ MAS NMR study", Microporous and Mesoporous Materials, Elsevier Science Publishing, New York, US, vol. 86, No. 1-3, Nov. 28, 2005, p. 31-37, XP005159928, ISSN: 1387-1811, paragraph [02.1], sample c) figures 2,3 sample c) figures 5,6.

Zhang Y, et al., "Synthesis and Catalysis of nanometer-sized bimodal mesoporous aluminosilicate materials" Catalysis Today, Elsevier, vol. 93-95, Sep. 1, 2004, p. 615-618, XP004549001, ISSN: 0920-5861, paragraph [02.1], [03.2] figure 3.

Tian P. et al., "Preparation of Ru metal nanoparticles in mesoporous materials: influence of sulfur on the hydrogenating activity", Microporous and Mesoporous Materials, Elsevier Science Publishing New York, US, vol. 60, No. 1-3, Jun. 19, 2003, p. 197-206, XP004430825, ISSN: 1387-1811, abstract, paragraph [03.1] figure 1.

* cited by examiner

CATALYST SUPPORT AND PROCESS FOR THE PREPARATION THEREOF

RELATED APPLICATIONS

This application is a divisional of U.S. application Ser. No. 12/674,202, filed Feb. 19, 2010, which is a U.S. national stage application under 35 U.S.C. §371 of International Application No. PCT/EP2008/061239 filed Aug. 27, 2008, which claims the benefit of the European application No. 07115255.7 filed on Aug. 30, 2007, the whole content of these applications being herein incorporated by reference.

BACKGROUND

This invention relates to a catalyst support and a process for the preparation thereof. In particular, this invention relates to a silica/alumina catalyst support which can be used with a catalytically active component to catalyst a variety of reactions, particularly but not exclusively hydrogenation reactions.

A wide variety of catalyst supports are known including those based on porous refractory oxides, such as silica. The use of silica gel support normally produces relatively poor results.

It is known to prepare amorphous silica-aluminas from aluminium salts such as aluminium chloride or aluminium sulfate and silicon sources such as sodium silicate (waterglass). Such a method is for example described in U.S. Pat. No. 4,988,659. The main disadvantages of such amorphous silica-aluminas, is the necessity to spray-dry the cogel mass to form spherical particles, and a high residual salt content, irrespective of the washing steps. Indeed, many anions such as $Cl^-$ and/or $(SO_4)^{2-}$ remain trapped in the silica-alumina structure, even after washing, while the corresponding cations, usually $Na^+$, are fixed into the silica-alumina structure.

Various documents have disclosed the combination of silica gel and alumina and these include U.S. Pat. No. 2,285,314 where silica gel is mixed with hydrous alumina to form a silica/alumina catalyst, and GB 1,223,878 where silica gel is mixed with an alumina source, such as sodium aluminate, at a pH of between 7.5 and 11 to produce a silica support with alumina particles precipitated thereon. These supports both result in a limited improvement in performance over pure silica.

Various other documents, such as GB 1,178,594, have disclosed the use of synthetic zeolites (alumino-silicate) as catalyst supports. Synthetic zeolites are crystalline solids. Synthetic zeolites are usually formed by a process of slow crystallization of a silica-alumina gel (obtained from finely divided pure silica and sodium aluminate) in the presence of alkalis and organic templates, followed by washing and spray drying. One of the important processes to carry out zeolite synthesis is sol-gel processing.

Zeolites give better results as catalyst support but are expensive to manufacture. Furthermore, synthetic zeolites usually consist of small particles (around 10 μm ). As a catalyst support usually has a size of around 100 μm, the zeolite particles (around 10 μm) must be agglomerated in bigger particles (around 100 μm), which is usually carried on using a binder. Such products have the disadvantage of being more sensitive to attrition compared to "one piece" products, such as those based on silica gel.

DETAILED DESCRIPTION OF THE DRAWINGS AND THE PRESENTLY PREFERRED EMBODIMENTS

An object of the present invention is to provide a catalyst support having improved properties, especially a high performance and a low attrition value. An object of the present invention is also to provide a simple process for the manufacture of such a catalyst support.

According to the present invention there is provided an amorphous catalyst support comprising at least:

(1) a first oxide selected from the group consisting of: silica, germanium oxide, titanium oxide, zirconium oxide or mixtures thereof, (2) a group 3 metal oxide, and (3) anions in an amount not greater than 10% by weight of the catalyst support, wherein the group 3 metal oxide is incorporated in the first oxide structure at the molecular level.

In particular, the group 3 metal oxide is typically present in a tetrahedral arrangement, shown by Nuclear Magnetic Resonance analysis. Especially, $^{27}Al$ solid-state NMR can be used to show the tetrahedral arrangement of the group 3 metal oxide, when group 3 metal oxide is alumina. Indeed, $^{27}Al$ NMR allows to discriminate between the different arrangements of the aluminium. The spectral region of 50-70 ppm, especially around 54 ppm, corresponds to tetrahedrally coordinated aluminium, the region around 0 ppm is assigned to octahedrally coordinated aluminium, the region around 30 ppm relates to pentahedral aluminium, and the region around—180 ppm corresponds to metallic aluminium. In the present invention, the expression "the group 3 metal oxide is present in a tetrahedral arrangement shown by NMR analysis" means that no other peaks, corresponding to metallic, pentahedral, or especially to octahedral aluminium, are present further to the $^{27}Al$ NMR analysis. Indeed, part of the octahedrally coordinated aluminium is NMR-silent due to the high anisotropy of these sites. Thus, according to the present invention, only NMR peaks of tetrahedral coordination should be present on the spectra. This does not exclude the presence of a few other arrangements, especially octahedral coordination, in the product, but such that the other arrangements would not be visible on the NMR spectra. $^{11}B$ magic-angle-spinning (MAS) NMR or $^{11}B$ solid-state NMR can be used to show the tetrahedral arrangement of the group 3 metal oxide, when group 3 metal oxide is boron oxide. $^{71}Ga$ solid-state NMR can be used to show the tetrahedral arrangement of the group 3 metal oxide, when group 3 metal oxide is gallium oxide.

Transmission electron microscopy (TEM) and/or scanning electron microscopy (SEM) coupled with energy dispersive X-ray spectrometry (EDX) show that the alumina is surprisingly not found only on the exterior surface of the silica gel beads (for example, as a coating) but also inside the silica gel beads. The catalyst support of the present invention is therefore quite homogeneous at a molecular level. Thus, the expression "incorporated in the first oxide structure at the molecular level" intends to mean that the second oxide is incorporated in the microscopic structure of the first one, and thus that the resulting catalyst support is homogeneous, by opposition to a first oxide on which a second oxide would have been deposited and/or precipitated.

The expression "amorphous" intends to denote a solid in which there is no long-range order of the positions of the atoms, in contrast to solids in which there is long-range atomic order which are called crystalline solids. Zeolites are crystalline solids. The "amorphous" or "crystalline" property of the catalyst supports of the present invention may be shown by X-ray diffraction spectrometry (XRD).

According to the present invention, anions optionally present in the catalyst support may be, for example, $Cl^-$, $(CO_3)^{2-}$, $(SO_4)^{2-}$, and/or $NO_3^-$. The associated cation may be, for example, $Na^-$. The amount of anions is usually at most 10% by weight of the catalyst support, preferably at most 8 wt %, more preferably at most 6 wt %, especially at most 5 wt %, with particular preference at most 3%, with higher preference at most 2.5 wt %. The amount of anions is usually at least 0.05% by weight of the catalyst support, in particular at least 0.5 wt %, more particularly at least 1 wt %, for example at least 1.5 wt %. The amount of cations is usually at most 10 wt %, preferably at most 5 wt %, more preferably at most 3 wt %, especially at most 2.5 wt %.

The amount of anions present in the catalyst support may be measured by any known method. Especially, total chlorine may be determined by the Wurzschmitt method (total oxidative decomposition with sodium peroxide and subsequent titration with 0.1 N $AgNO_3$); sulfur concentration may be determined by Inductively Coupled Plasma Optical Emission Spectrometry (ICP-OES) after closed vessel microwave total digestion of the sample; carbon and nitrogen concentrations may be determined by elemental analysis, for example using a VarioEL apparatus (Elementar). It can be assumed that these elements correspond to the respective anions. Especially, Cl corresponds to $Cl^-$, N corresponds to $NO_3^-$, C corresponds to $(CO_3)^{2-}$, and S corresponds to $(SO_4)^{2-}$. The values obtained for Cl, N, C and S can thus be converted into the amounts of the corresponding anions.

The group 3 metal oxide can be selected from the group consisting of alumina, boron oxide, and gallium oxide, preferably from alumina and gallium oxide. An especially preferred embodiment comprises alumina.

The first oxide advantageously comprises silica, especially amorphous silica such as silica gel beads, or diatomaceous earth.

Silica gel beads are especially preferred. The silica gel beads can have an average diameter in the range of from 20 to 4000 μm.

For example, for a fixed bed catalyst, the silica gel beads may have an average diameter in the range of from 500 to 4000 μm, preferably of from 1000 to 3000 μm, for example of from 2000 to 2500 μm.

In another embodiment, for a fluid bed catalyst, the silica gel beads may have an average diameter in the range of from 20 to 500 μm, preferably of from 30 to 300 μm, more preferably of from 50 to 200 μm, with particular preference of from 90 to 140 μm, typically of from 100 to 130 μm, especially of from 110 to 120 μm. Silica gel beads having a diameter less than 40 μm are normally not present; indeed typically beads of a diameter of less than 50 μm are not used, especially beads with a diameter less than 63 μm. The BET surface area of the silica gel beads can be of from 100 to 800 $m^2/g$, typically of from 200 to 700 $m^2/g$, especially of from 300 to 600 $m^2/g$. The pore size of the silica gel beads may be of from 1 to 30 nm, preferably of from 2.5 to 25 nm, especially of from 5 to 20 nm.

The group 3 metal oxide is usually present in the catalyst support according to the present invention in an amount of at least 1%, preferably at least 2%, more preferably at least 3%, values of around 5% giving good results. The amount of group 3 metal oxide in the catalyst support according to the present invention is in general of at most 50%, especially at most 30%, in particular at most 20%, for example at most 10%. A suitable range for the amount of group 3 metal oxide is from 1 to 50%, for example around 5 to 10%. The amount of group 3 metal oxide is expressed in percent by weight of the catalyst support.

The catalyst support of the present invention is normally used with a catalytically active component to form a catalyst.

Thus the invention also provides a catalyst comprising a catalytically active component and a support as described herein.

The catalytically active component may vary widely depending on the intended use of the catalyst. Supports in accordance with the present invention, may be used with active metals, especially transition metals, such as vanadium or molybdenum, in particular with precious metals such as one selected from the group consisting of: platinum, palladium, iridium, rhodium, gold, silver or mixtures thereof.

The catalyst according to the present invention can be prepared by any known method using the catalyst support of the present invention, as disclosed in Ullmann's Encyclopedia of Industrial Chemistry, Chapter "Heterogeneous Catalysis and Solid Catalysts" (DOI: 10.1002/14356007.a05_313, Article Online Posting Date: Jan. 15, 2003), especially pages 42 to 44. For example, the catalyst may be prepared by any known method of impregnation, adsorption, precipitation, or reductive deposition.

According to a further aspect of the present invention, there is provided a process for the preparation of the catalyst support, the process comprising:

(a) mixing a first oxide selected from the group consisting of: silica, germanium oxide, titanium oxide, zirconium oxide or mixtures thereof, preferably silica gel beads or diatomaceous earth; with an anhydrous source of a group 3 metal oxide, and water, at a pH above 11, thus forming a suspension, (b) optionally washing the catalyst support with water, (c) separating the catalyst support from the water, (d) optionally drying and/or calcining the catalyst support.

Typically the process according to said further aspect of the invention results in the catalyst support according to earlier aspects of the present invention.

Typically the first oxide according to said further aspect of the invention comprises the first oxide as described herein.

The first metal oxide can be used in the form of an aqueous suspension and the anhydrous source of the group 3 metal oxide can be used as an aqueous solution.

The temperature in step (a) is in general at least 30° C., in particular at least 50° C., values of at least 70° C. giving good results. The temperature in step (a) is usually at most 95° C., in many cases at most 90° C., values of at most 85° C., and especially of at most 80° C., being common. Suitable ranges for the temperature in step (a) are from 30 to 90° C., preferably from 55 to 85° C., more preferably from 70 to 80° C., for example around 75° C.

The water used in step (a) is usually demineralised water.

The pH of the mixture in step (a) is above 11, preferably at least 11.5. The pH of the mixture in step (a) is usually at most 12.5, in particular at most 12. For example, the pH of the mixture in step (a) is of from 11.5 to 12. The pH of the mixture in step (a) may be adjusted by means of pH modifying compounds. Especially, if the pH has to be increased, alkali hydroxide, such as sodium hydroxide or potassium hydroxide, or suitable alternative bases may be added. The mixture in step (a) is usually agitated with a mechanical stirrer in order to maintain the silica gel as a suspension.

The mixture in step (a) may be stirred for from 5 to 90 mins, typically for from 10 to 75 mins, preferably from 15 to 60 mins, especially from 15 to 30 mins, for example around 20 mins.

The term "anhydrous" means a substance which does not contain water. Thus alumina gel for example is hydrous, not anhydrous. The anhydrous source may indeed be provided within a solution or a suspension but is nevertheless classed as anhydrous.

The anhydrous source of the group 3 metal oxide can comprise a metal-[group 3 metal] oxide. For example where the group 3 metal oxide comprise alumina, the anhydrous source of the group 3 metal oxide may be sodium aluminate. This is in marked contrast to common techniques to prepare, for example, silica/alumina, where aluminium salts are commonly used as the alumina source, requiring a calcination step to oxidise the metal salt.

According to this further aspect of the present invention, the resulting product from step (a) may be washed at least once with water, in order to eliminate small particles and/or impurities, for example alkali derivatives such as NaOH or sodium silicate. The water is usually demineralised water. In a further embodiment, the resulting product from step (a) may be washed more than once with water, for example, the resulting product from step (a) may be washed three times with water. According to another further embodiment, the supernatant water present in the resulting product from step (a) may only be replaced by fresh water.

The separation of the catalyst support from the water in step (c) can be conducted following any known method in the art, for example by decantation, filtration, and/or centrifugation.

The catalyst support resulting from step (c) may optionally be dried and/or calcined in step (d), according to any known method in the art. If the catalytically active component is added to the support in water, then conveniently no drying or calcination of the support is required before addition of the catalytically active component especially where the group 3 metal source is an oxide.

For example, the catalyst support resulting from step (c) may be dried using an air circulating oven, for example at a temperature of from 100 to 200° C., at atmospheric pressure. It can also be dried in an oven under reduced pressure. The catalyst support may also be calcined, for example at a temperature around 400° C. Thus the process may include a step (d), (d) comprising drying the catalyst support. Although calcination may also be performed, preferred embodiments are not heated to a temperature above 200° C. before addition of a catalytically active component.

The process according to this further aspect of the invention has the advantage to be simple, therefore leading to the catalyst support according to embodiments of the invention in an easy way. This process also has the advantage to lead to a clean product containing few impurities, which does not need expensive washing. The product obtained according to this further aspect of the invention may contain less than 15% impurities, preferably less than 10% impurities, more preferably less than 5% impurities, for example less than 2% by weight of impurities. The percentage of impurities is expressed as a percentage by weight of the catalyst support. Impurities which can be present in the catalyst support of the present invention are, for example sodium salts such as sodium silicate.

The invention also provides a catalyst support prepared by
(a) mixing a first oxide selected from the group consisting of: silica, germanium oxide, titanium oxide, zirconium oxide or mixtures thereof, preferably silica gel beads or diatomaceous earth, with an anhydrous source of a group 3 metal oxide, and water, at a pH above 11, thus forming a suspension,
(b) optionally washing the catalyst support with water,
(c) separating the catalyst support from the water,
(d) optionally drying and/or calcining the catalyst support.

The invention also provides the use of a catalytically active component and the catalyst support described herein as a catalyst.

The catalytically active component may vary widely depending on the intended use of the catalyst. Supports in accordance with the present invention, may be used with active metals, especially transition metals, such as vanadium or molybdenum, in particular with precious metals such as platinum, palladium, iridium, rhodium, silver or gold, or mixtures thereof. Such catalysts are useful to catalyst reduction reactions, especially for hydrogenation reactions such as hydrogenation of hydrocarbons or nitrobenzene, or to catalyst oxidation reactions, such as the oxidation of propylene into acrolein.

The catalyst support according to the present invention is especially suitable for the preparation of hydrogenation catalysts used in the well-known alkylanthraquinone(s), or AO process (see, for example, "Ullmann's Encyclopedia of Industrial Chemistry, Fifth Edition, 1989, Volume 3, pages 447-457"). The expression "alkylanthraquinone process" is intended to denote a process for producing an aqueous hydrogen peroxide solution which consists in subjecting a working solution of at least one alkylanthraquinone and/or of at least one tetrahydroalkylanthraquinone to a hydrogenation step, in a diluent, to produce one or more alkylanthrahydroquinones and/or alkyltetrahydroanthrahydroquinones. The working solution leaving the hydrogenation step is then subjected to an oxidation with oxygen, air or oxygen-enriched air to give hydrogen peroxide and to reform the alkylanthraquinones and/or alkyltetrahydroanthraquinones. The hydrogen peroxide formed is then separated from the working solution by means of an extraction step, for example using water, the hydrogen peroxide being recovered in the form of a crude aqueous hydrogen peroxide solution. The working solution leaving the extraction step is then recycled into the hydrogenation step in order to recommence the hydrogen peroxide production cycle.

The term "alkylanthraquinones" is intended to denote, for example, 9,10-anthraquinones substituted in position 1, 2 or 3 with at least one alkyl side chain of linear or branched aliphatic type comprising at least one carbon atom. These alkyl chains usually comprise less than 9 carbon atoms and preferably less than 6 carbon atoms. Examples of such alkylanthraquinones are 2-ethylanthraquinone, 2-isopropylanthraquinone, 2-sec- and 2-tert-butylanthraquinone, 1,3-, 2,3-, 1,4- and 2,7-dimethylanthraquinone, and 2-iso- and 2-tert-amylanthraquinone, and mixtures of theses quinones.

The term "alkyanthrahydroquinones" is intended to denote the 9,10-hydroquinones corresponding to the 9,10-alkyanthraquinones specified above.

The present invention therefore also relates to a catalyst comprising the catalyst support of the present invention and palladium as catalytically active component for the catalysis of hydrogenation reactions in the alkylanthraquinone(s) process for the manufacture of hydrogen peroxide.

The present invention also relates to the use of a catalytically active component and the catalyst support of the present invention as a catalyst to catalyst hydrogenation reactions in the alkylanthraquinone(s) process for the manufacture of hydrogen peroxide.

Having described the invention in general terms, specific embodiments thereof will now be illustrated by way of example only.

EXAMPLES $^{27}$Al Nuclear Magnetic Experiments ($^{27}$Al NMR)

$^{27}$Al NMR experiments on the catalyst supports were run on a spectrometer at 78.2 MHz, with a pulse of 18°, a pulse delay of 1 s, and a spinning rate of 8 kHz.

The reference was Al(NO$_3$)$_3$. The purpose of these experiments was to show the tetrahedral and/or octahedral arrangement of the Al. Indeed, these two kinds of aluminium shows different peaks in $^{27}$Al NMR : the spectral region of 50-70 ppm, especially around 54 ppm, corresponds to tetrahedrally coordinated aluminium, while the region around 0 ppm is assigned to octahedrally coordinated aluminium. Other peaks corresponding to aluminium species could be present around—180 ppm (metallic aluminium) or around 30 ppm (pentahedral aluminium).

X-ray Diffraction Spectrometry (XRD)

The catalyst supports were analyzed by XRD using a Philips PW1050 theta/2-theta Bragg-Brentano type powder goniometer, in combination with a Philips PW1729 X-ray generator unit, equipped with a Cu anode X-ray tube, and a Philips PW1710 diffractometer control unit. Prior to analysis the samples were pressed slightly into a flat rectangular sample holder. The diffractogram was recorded from 1 to 70 degrees 2-theta during approx. 1 hour (1.2 °2-theta/min) with an anode current of 40 mA and a tension of 40 kV. The diffractograms were qualitatively evaluated with the identification program Traces v6.

Energy Dispersive X-ray Spectrometry (EDX)

EDX mapping was used to assess the dispersion homogeneity of the different elements, and especially aluminium in the catalyst support.

In order to establish an EDX mapping, after recording an XRD spectrum and a Scanning Electron Microscopy (SEM) or Transmission Electron Microscopy (TEM) image of the region of interest (ROI), the acquisition parameters are selected as a function of the sample and the microscope settings (for example magnification). These include the number of pixels in the image (typically, 128×128 pixels or 256× 256 pixels), the energy windows corresponding to the peaks of the elements to be mapped, the dwell time (acquisition time per pixel) and the number of scans.

The SEM-EDX analysis was conducted using a Scanning Electron Microscope (Gemini Leo 982) associated to an EDX detector (Oxford).

Prior to the analysis, the sample was embedded into polymethylmethacrylate (PMMA), the surface of the sample was smoothed using a Reichert Supernova Ultramicrotome, and metallized with Pt/Pd using a Cressington Sputter Coater.

The TEM-EDX analysis was conducted using a Transmission Electron Microscope (Zeiss EM910) associated to an EDX detector (Oxford).

Prior to the analysis, the sample was embedded into polymethylmethacrylate (PMMA) and thin sections of samples were cut using a Reichert Supernova Ultramicrotome.

SEM-EDX was used for low magnification mappings of the catalyst supports while TEM-EDX was used for high magnifications.

Wavelength Dispersive X-Ray Fluorescence Spectrometry (WD-XRF)

WD-XRF measurements were conducted on the catalysts using a PANalytical PW2404 XRF analyzer equipped with a PW 2540 VRC sample changer and UniQuant® software package (Omega Data Systems).

Prior to analysis the samples were pressed in Chemplex® aluminium sample cups, using a Herzog TP40/2D press.

Amount of Anions

Total chlorine was determined according to the Wurzschmitt method, namely after total oxidative decomposition of the sample with sodium peroxide and subsequent titration with 0.1 N AgNO$_3$.

Sulfur concentration was determined by Inductively Coupled Plasma Optical Emission Spectrometry (ICP-OES) after closed vessel microwave total digestion of the sample.

Carbon and nitrogen concentrations were determined by elemental analysis using a VarioEL apparatus (Elementar).

Palladium Assay by Gravimetric Method

Palladium is extracted from the catalyst by mild boiling at 80° C. for 15 minutes in a dilute hydrogen chloride solution containing hydrogen peroxide as oxidant (3g of catalyst, 50 ml of demineralised water, 10 ml of concentrated HCl solution, and 1 ml of H$_2$O$_2$). The carrier is separated off by filtration and washing of the insoluble fraction with water. After solubilisation, the solution containing the palladium is treated with 5 ml of NaOH (10 N) to reach an acidity of around 0.25 N. The mixture is heated until boiling, 20 ml of dimethyl glyoxime at 1% in methanol is added with vigorous mix with glass stick, and the heating is continued for 30 minutes. The mixture is cooled for 2 hours, then the precipitate is filtered, washed with 5×20 ml of hot acidified water and 2×10 ml of methanol, and dried in an oven at 110° C. for 30 min. The palladium content (g/kg) is calculated according to the following formula:

Palladium content (g/kg)=weight of precipitate (g)× 0.3167×1000/weight of sample The constant 0.3167 corresponds to the ratio of the molecular weight of palladium and the dimethyl glyoxime precipitate.

Example 1

Preparation of a Catalyst Support and of a Palladium Catalyst According to the Invention 100g of silica gel beads was added to a 2 l reactor vessel along with 500 ml of demineralised water, therefore forming a suspension of silica gel beads in water. The silica gel beads were double sieved quality with particle size distribution of from 63 to 150 μm, and an average diameter of from 110 to 120 μm. The pores size was in the range of 5-20 nm and BET surface area was 300-600 m$^2$/g. Preferred silica specification is set out in Table 1 below.

TABLE 1

| Product description | Silica Gel |
|---|---|
| Typical properties: | |
| Appearance | White, free flowing powder; translucid under microscope |

TABLE 1-continued

| Product description | Silica Gel |
|---|---|
| Shape | Minimum 80% spherical shape, tending to 100% spherical shape |
| Bulk density | 350-550 g/l |
| Specific surface area | 300-500 m²/g |
| pH of 5% slurry in water | 5-9 |
| Loss on drying (200° C.) | Maximum 10% |
| Typical chemical composition | |
| $SiO_2$ | >98% |
| $Al_2O_3$ | <1% |
| Iron ($Fe_2O_3$) | <0.05% |
| $Cr_2O_3$ | <0.05% |
| Particle size | |
| <63 µmISO or 230 US Mesh | Max 2% |
| <250 µm ISO or 60 US Mesh | Min 95% |

21.7 g of sodium aluminate solution (23% alumina—19% $Na_2O$) was added to the silica gel beads suspension, forming a suspension. The resulting catalyst support thus contained a theoretical amount of alumina of around 5% by weight. The mixture was agitated at around 200 rpm to maintain a suspension and heated from ambient temperature to 60° C. over 30 minutes and then maintained at 60° C. for 1 hour. The remaining liquid was then removed by decantation. The resulting catalyst support was washed three times with 500 ml of demineralised water each time, primarily to remove excess alkalinity. The resulting catalyst support was then dried in an air circulating oven at a temperature of around 110° C. under atmospheric pressure.

The resulting catalyst support was analysed with $^{27}Al$ NMR, XRD and SEM-EDX and TEM-EDX mappings.

XRD analysis of the catalyst support showed that the catalyst support is amorphous. No crystalline form of silica or alumina was observed.

SEM-EDX mapping and TEM-EDX analysis showed that the alumina is surprisingly not only found on the exterior surface of the silica gel but also inside it. The catalyst support is therefore quite homogeneous.

Figure 1:
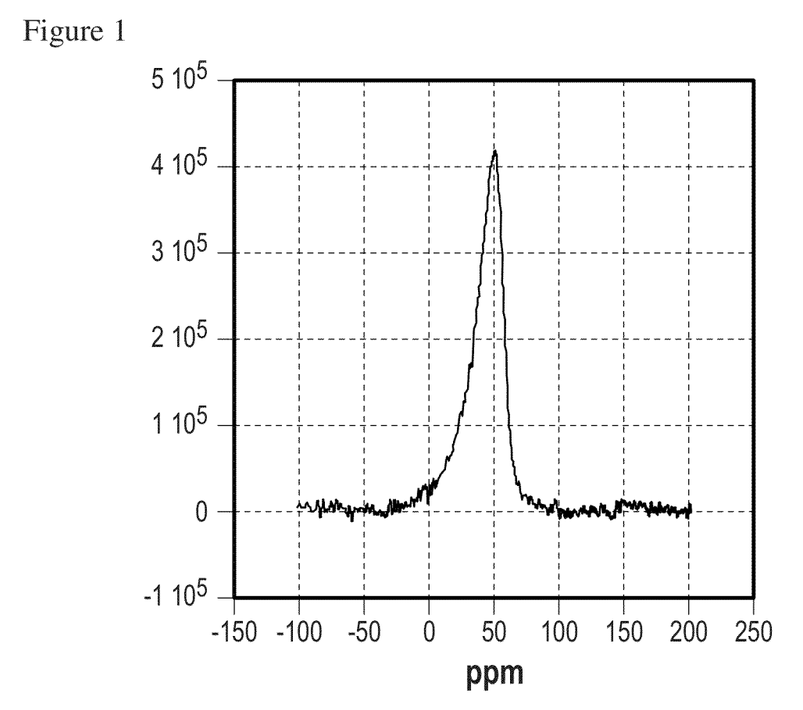
FIG. 1 is a graphical result of an NMR analysis of one embodiment of the catalyst support.

$^{27}Al$ NMR analysis of the catalyst support showed that the alumina is present in a tetrahedral arrangement similar to that found in a zeolite (peak around 54 ppm) and that no peak corresponding to alumina in a octahedral arrangement could be identified (no peak around 0 ppm) (FIG. 1). The number of scans was 8192.

The analysis of the catalyst support showed Cl, N, C and S total amounts below the detection limit of the methods, that is to say below 0.5 g/kg for total chlorine, below 1 g/kg for nitrogen and carbon, and below 1.5 g/kg for sulfur. It can be considered that these elements correspond respectively to $Cl^-$, $NO_3^-$, $(CO_3)^{2-}$, and $(SO_4)^{2-}$. These values can thus be converted to amounts of Cl below 0.5 g/kg, $NO_3^-$ below 4.4 g/kg, $(CO_3)^{2-}$ below 5 g/kg, and $(SO_4)^{2-}$ below 1.5 g/kg, which correspond to an anion content below 11.4 g/kg, or below 1.14 wt %.

A catalyst comprising 2% palladium was prepared using the catalyst support described above. The palladium was deposited by precipitating palladium on the catalyst support from a palladium salt solution in the presence of an alkali. The obtained catalyst was then washed three times with water and dried at around 150° C. under a mixture of 20% $H_2$ in nitrogen.

WD-XRF analysis of the catalyst showed a content of 2.4 wt % of sodium, 3 wt % of aluminium and 41 wt % of silicon.

The amount of palladium in the catalyst, determined by a gravimetric method, was of 20.1 g/kg.

Figure 2:
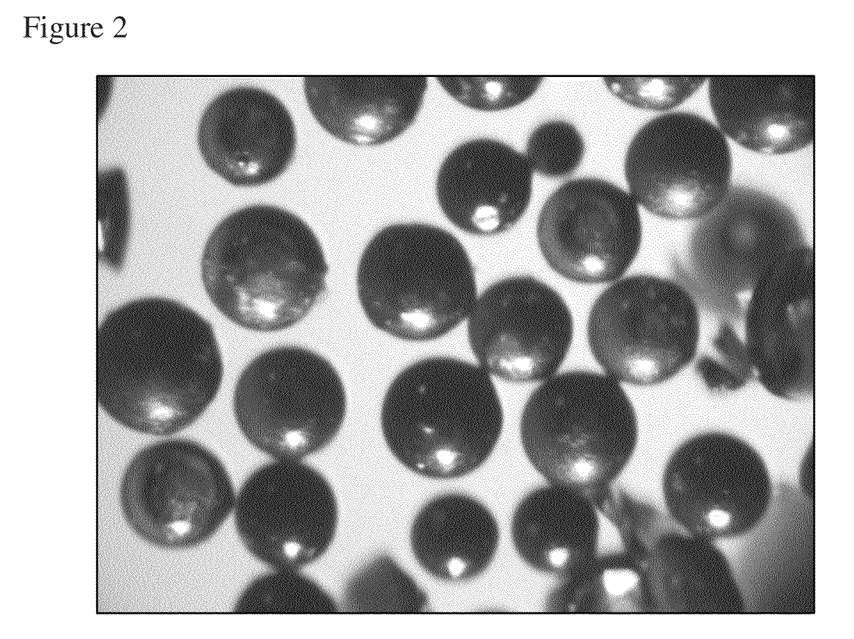
FIG. 2 is an optical microscope photo of one embodiment of the catalyst.

Optical microscope analysis of the catalyst showed that all catalyst support grains were covered with palladium (black aspect of the grains) (FIG. 2).

Examples 2 to 5

Preparation of Catalyst Supports Comprising Various Amounts of Aalumina

The procedure of Example 1 was reproduced but with different amounts of sodium aluminate, corresponding to alumina amounts of 2.5% by weight of the catalyst support (Example 2), 10% (Example 3), 15% (Example 4) and 25% (Example 5).

Figure 3:
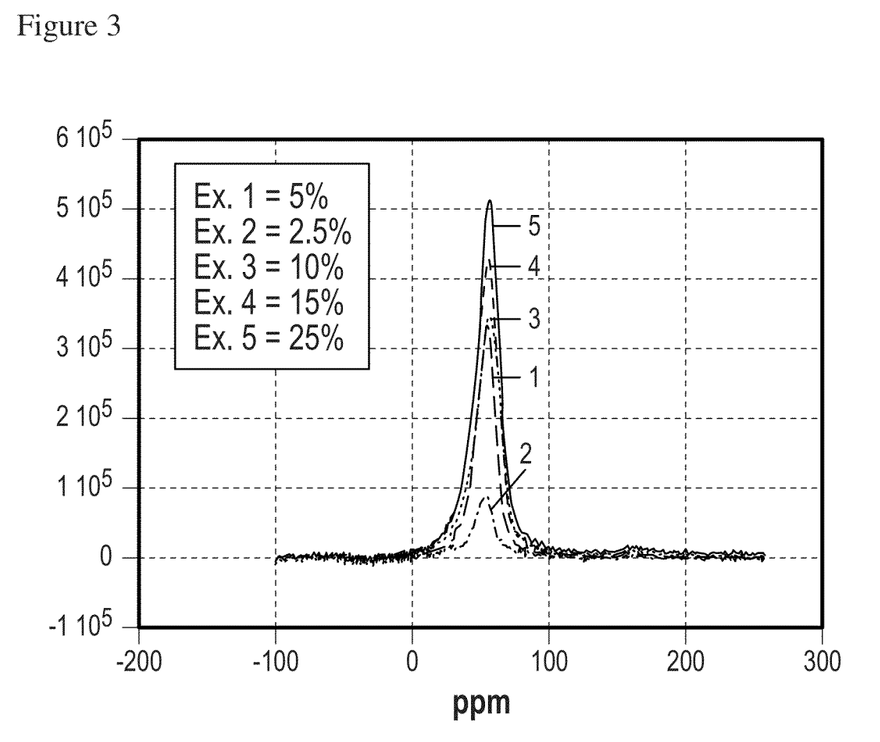
FIG. 3 is a graphical result of an NMR analysis of several embodiments of the catalyst support.

$^{27}Al$ NMR analysis of the catalyst supports of Example 2 to 5 showed that the alumina is present in a tetrahedral arrangement similar to that found in a zeolite (peak around 54 ppm) and that no peak corresponding to alumina in a octahedral arrangement could be identified (no peak around 0 ppm), even for alumina amounts as high as 25% by weight of the catalyst support (FIG. 3).

Example 6 (Comparative)

Preparation of a Catalyst Support and of a Palladium Catalyst at a pH<11

The catalyst support of Example 6 was prepared according to Example 1, except that the pH of the silica gel suspension was adjusted to a value between 8 and 9.3 with 2N sulphuric acid. The sulphuric acid was added to the reaction mixture simultaneously with the addition of the sodium aluminate solution, such that the pH was maintained in a range between 8 and 9.3 during the whole reaction.

Figure 4:
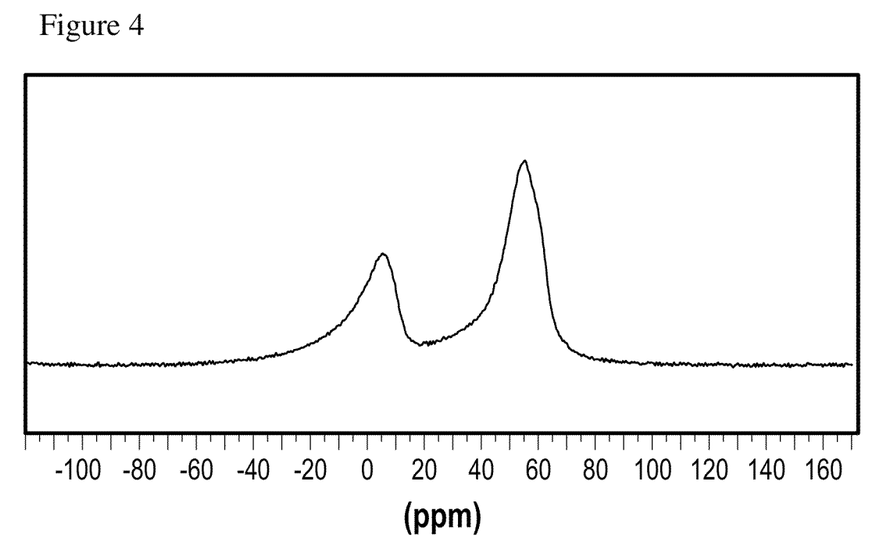
FIG. 4 is a graphical result of an NMR analysis of a comparative example of the catalyst support.

$^{27}Al$ NMR analysis of the catalyst support of Example 6 showed that the alumina is present in both tetrahedral (peak around 54 ppm) and octahedral arrangements (peak around 0 ppm) (FIG. 4). The number of scans was 48000.

2% of palladium by weight of the catalyst were then deposited onto the catalyst support according to the same process as in Example 1.

WD-XRF analysis of the catalyst showed a content of 1.7 wt % of sodium, 3.7 wt % of aluminium and 41 wt % of silicon, which is comparable to the results obtained for the catalyst of Example 1.

The amount of palladium in the catalyst, determined by gravimetric measurement, was of 18.7 g/kg.

Figure 5:
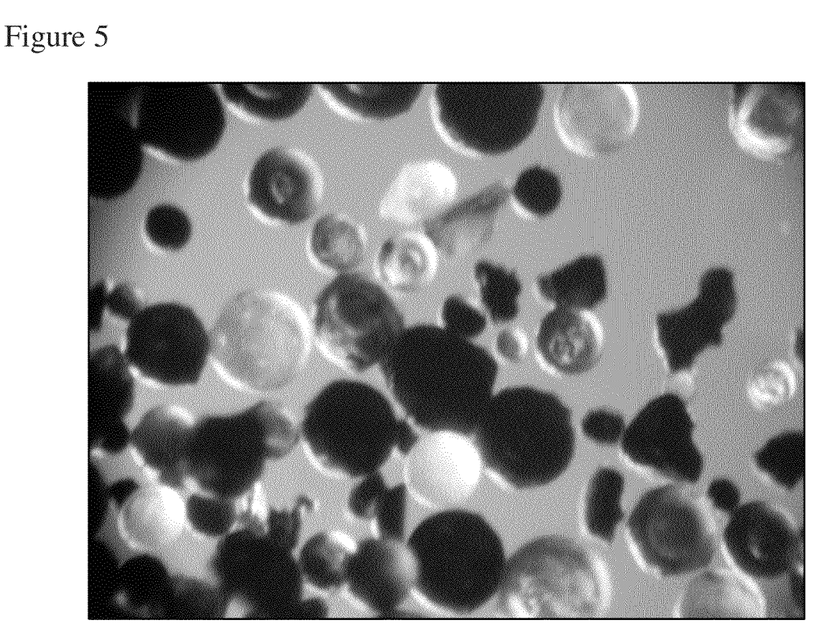
FIG. 5 is an optical microscope photo of a comparative example of the catalyst.

Optical microscope analysis of the catalyst showed that there was no palladium deposit on some of the catalyst support grains, thus a less good fixation of the palladium onto the catalyst support occurred when using the catalyst support prepared according to Comparative Example 6 (FIG. 5).

Figure 6:
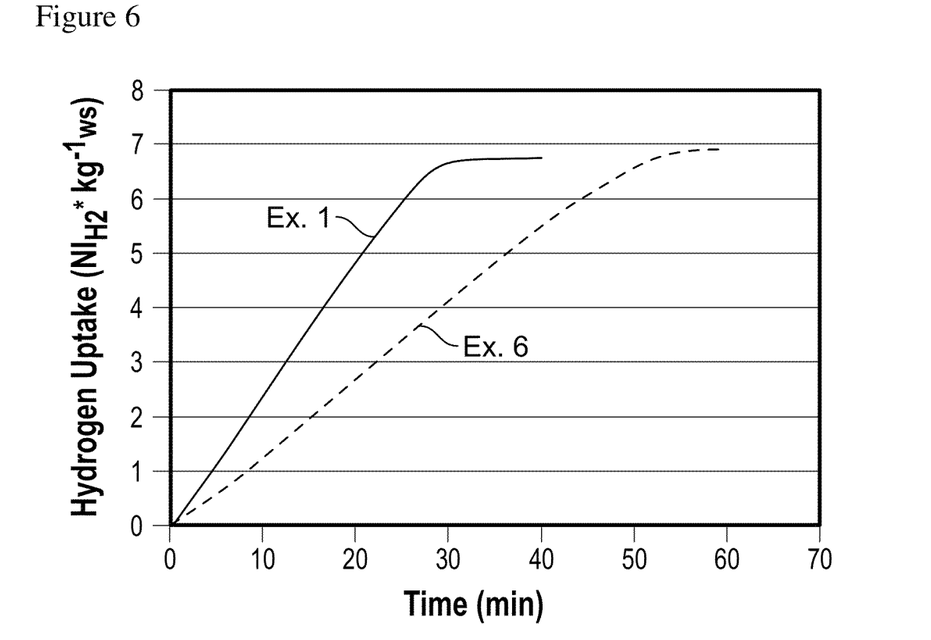
FIG. 6 is a graphical result of hydrogen gas uptakes comparing two catalysts used for hydrogenation reaction of nitrobenzene.

Comparison of the Activity of the Catalysts Prepared According to Examples 1 and 6 in the Hydrogenation of Nitrobenzene into Aniline The catalysts prepared according to Examples 1 and 6 were tested in the hydrogenation reaction of nitrobenzene into aniline. The reaction was conducted in a non-polar solvent, with a concentration of nitrobenzene of 20 g/l, at a temperature of 55° C., under a pressure of 1150 mbars (mbar absolute) or 150 mbar (mbar relative), and under stirring (gaseous effect turbine). The hydrogen gas uptake (expressed in normal litres per kg of working solution) was measured for the two catalysts (FIG. 6). This clearly shows that better results are obtained when using the catalyst based on the support of the present invention (Example 1), rather than a catalyst based on a comparative support (Example 6).

Comparison of the Activity of the Catalysts Prepared According to Examples 1 and 6 in the Hydrogenation of Alkylanthraquinone into Alkylanthrahydroquinone and Alkyltetrahydroanthraquinone The hydrogenation of alkylanthraquinone into alkylanthrahydroquinone and alkyltetrahydroanthraquinone was conducted in a mixture of a polar solvent (20 wt %) and of a non-polar solvent (80 wt %) saturated with water, at a temperature of 55° C., under a pressure of pressure of 1150 mbars (mbar absolute) or 150 mbar (mbar relative) of hydrogen gas. The concentration of the alkylanthraquinone was about 70 g/kg of working solution (mixture of the solvents) and the amount of catalyst was about 0.6% by weight of working solution.

Figure 7:
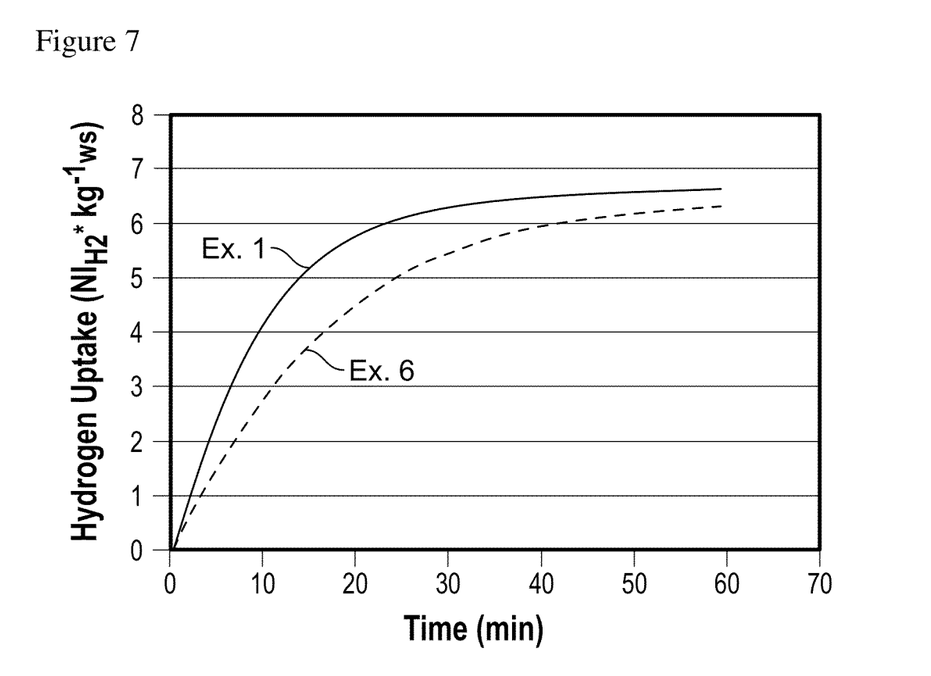
FIG. 7 is a graphical result of hydrogen gas uptakes comparing two catalysts used for hydrogenation reaction of alkylanthraquinone.

The hydrogen gas uptake (expressed in normal litres per kg of working solution) was measured for the two catalysts (FIG. 7). This clearly shows that better results are obtained when using the catalyst based on the support of the present invention (Example 1), rather than a catalyst based on a comparative support (Example 6).

The results obtained with the catalysts prepared according to Examples 1 and 6 are summarized in Table 2 below. The rates of conversion of alkylanthraquinone into alkylanthrahydroquinone and of alkylanthrahydroquinone into alkyltetrahydroanthraquinone are expressed respectively in $10^{-4}$ $g^{-1}$ $s^{-1}$ and $10^{-6}$ $g^{-1}$ $s^{-1}$ ($g^{-1}$ corresponding to "by gram of catalyst").

TABLE 2

|  | Catalyst of Example 1 | Catalyst of Example 6 |
|---|---|---|
| Rate of conversion of alkylanthraquinone into alkylanthrahydroquinone ($10^{-4}$ $g^{-1}$ $s^{-1}$) | 3.87 | 1.61 |
| Rate of conversion of alkylanthrahydroquinone into alkyltetrahydroanthraquinone ($10^{-6}$ $g^{-1}$ $s^{-1}$) | 1.33 | 1.03 |

Improvements and modifications may be made without departing from the scope of the invention.

The invention claimed is:

1. A process for the preparation of a catalyst support, the process comprising:
   (a) mixing silica gel beads or diatomaceous earth with an anhydrous source of alumina and water, at a pH above 11, thus forming a suspension of the catalyst support in water,
   (b) optionally, washing the catalyst support with water,
   (c) separating the catalyst support from the water, and
   (d) optionally, drying and/or calcining the catalyst support.

2. A process as claimed in claim 1, wherein the temperature in step (a) is in the range of from 30 to 90° C.

3. The process as claimed in claim 1, wherein the temperature in step (a) is in the range of from 55 to 85° C.

4. The process as claimed in claim 1, wherein the anhydrous source of alumina comprises a metal-alumina.

5. The process as claimed in claim 4, wherein the anhydrous source of alumina comprises sodium aluminate.

6. The process as claimed in claim 1, wherein the mixture in step (a) is stirred for 5 to 90 minutes.

7. The process as claimed in claim 1, wherein the mixture in step (a) is stirred for 15 to 60 minutes.

8. The process as claimed in claim 1, wherein the catalyst support comprises anions in an amount not greater than 10% by weight of the catalyst support, and wherein the alumina is incorporated in the silica gel beads or diatomaceous earth at the molecular level.

9. The process as claimed in claim 8, wherein the alumina is present in a tetrahedral arrangement, shown by $^{27}$Al NMR analysis, and wherein no other peaks are shown by $^{27}$Al NMR analysis.

10. The process as claimed in claim 1, wherein the average diameter of the silica gel bead is of from 20 to 4000 μm.

11. The process as claimed in claim 1, wherein the concentration of the alumina is of from 1 to 50% by weight of the catalyst support.

12. The process as claimed in claim 8, wherein the anions are selected from Cl$^-$, (CO$_3$)$^{2-}$, (SO$_4$)$^{2-}$, NO$_3^-$ and mixtures thereof.

13. The process as claimed in claim 8, wherein the amount of anions is of at most 5 wt %.

14. The process as claimed in claim 8, wherein the amount of anions is of at most 3 wt %.

15. The process as claimed in claim 8, wherein the amount of anions is of at most 2.5 wt %.

16. A process for making a catalyst, said process comprising making a catalyst support as claimed in claim 1, and adding a catalytically active component selected from the group consisting of: platinum, palladium, iridium, rhodium, gold, silver and mixtures thereof.

17. The process according to claim 16, wherein the catalytically active component is palladium.

18. A process for making a catalyst, said process comprising making a catalyst support as claimed in claim 8, and adding a catalytically active component selected from the group consisting of: platinum, palladium, iridium, rhodium, gold, silver and mixtures thereof.

19. The process according to claim 18, wherein the catalytically active component is palladium.

20. A process to catalyse reduction reactions, including hydrogenation reactions for the manufacture of hydrogen peroxide, the process comprising reacting reactants in the presence of a catalyst made according to a process as claimed in claim 16.

* * * * *